United States Patent [19]

Shawl et al.

[11] Patent Number: 5,227,483
[45] Date of Patent: Jul. 13, 1993

[54] PROCESS FOR RECOVERY OF AMINES AND VOLATILE ACIDS FROM AMINE SALTS

[75] Inventors: Edward T. Shawl, Wallingford; Haven S. Kesling, Jr., Drexel Hill, both of Pa.

[73] Assignee: ARCO Chemical Technology, L.P., Wilmington, Del.

[21] Appl. No.: 814,543

[22] Filed: Dec. 30, 1991

[51] Int. Cl.$^5$ .............................. C07C 209/84
[52] U.S. Cl. ........................ 564/497; 564/437
[58] Field of Search ..................... 564/497, 437

[56] References Cited

U.S. PATENT DOCUMENTS

| | | | |
|---|---|---|---|
| 3,213,143 | 10/1965 | Fallstad | 564/497 |
| 3,337,630 | 8/1967 | Moke et al. | 260/583 |
| 3,410,906 | 11/1968 | Simpson | 260/583 |
| 3,471,562 | 10/1969 | Wakeman et al. | 260/583 |
| 3,849,496 | 11/1974 | Forster | 260/583 |
| 3,898,259 | 8/1975 | Hearsey | 260/453 P |
| 4,871,871 | 10/1989 | Shawl et al. | 560/344 |
| 4,873,364 | 10/1989 | Shawl et al. | 560/344 |
| 4,883,908 | 11/1989 | Shawl et al. | 560/344 |

Primary Examiner—Robert Gerstl
Attorney, Agent, or Firm—Jonathan L. Schuchardt

[57] ABSTRACT

A process for recovering both an amine and a volatile acid from an amine salt is disclosed. In the process, the amine salt is reacted with a non-volatile acid to liberate the volatile acid. Thermal decomposition of the resulting amine/non-volatile acid salt liberates the amine.

20 Claims, No Drawings

PROCESS FOR RECOVERY OF AMINES AND VOLATILE ACIDS FROM AMINE SALTS

FIELD OF THE INVENTION

The invention relates to amine and acid recover from amine salts. In particular, the invention is a process for recovering amines and volatile acids from amine salts using non-volatile acids.

BACKGROUND OF THE INVENTION

Amine salts having anions derived from volatile acids are produced as by-products from a number of industrially important reactions. For example, N-aryl-N',N'-dialkylureas can be cracked in the presence of hydrochloric acid (U.S. Pat. No. 3,898,259), organic sulfonic acids (U.S. Pat. No. 4,883,908), tertiary amine hydrohalide salts (U.S. Pat. Nos. 4,871,871 and 4,873,364), and other promoters to give aryl isocyanates. Dialkylammonium salts are typically the by-products from such reactions. In these urea cracking processes, and in other industrial processes that generate amine salts, it is desirable to recover both the amine and the volatile acid from the ammonium salt for reuse in the process.

Unfortunately, few economical and satisfactory methods for recovering amines and acids from amine salts are known. Most of the known methods focus on recovery of a valuable amine from an amine salt by reacting the amine salt with a less valuable amine or an alkali metal or alkaline earth metal hydroxide or carbonate in solution. For example, U.S. Pat. No. 3,471,562 teaches a process for making aliphatic tertiary amines by reacting a tertiary amine hydrohalide salt with an aqueous metal hydroxide to liberate the tertiary amine. Unfortunately, such processes require costly disposal of inorganic by-product wastes. U.S. Pat. No. 3,849,496 teaches a method for preparing amines by heating an amine hydrohalide with ammonia in an organic solvent. In this process, a valuable amine is recovered, but another amine salt is generated.

A conceptually desirable way to recover both acid and amine from amine salts is to thermally decompose the salt. Unfortunately thermal decomposition is not practical if a volatile acid is generated because the acid and amine rapidly recombine in the vapor phase to regenerate the salt.

SUMMARY OF THE INVENTION

The invention is a process for recovering an amine and a volatile acid from an amine salt. The process comprises: (a) reacting an amine salt with a non-volatile acid to form an amine/non-volatile acid salt while liberating the volatile acid; and (b) heating the amine/non-volatile acid salt at a temperature effective to liberate the amine.

DETAILED DESCRIPTION OF THE INVENTION

The amine salts used as starting materials for the process of the invention are the reaction products of ammonia or a primary, secondary, or tertiary amine with a volatile acid.

Suitable amine salts are derived from ammonia and any primary, secondary, or tertiary amine. The amine moiety has from 0 to 3 linear, branched, or cyclic alkyl, aryl, or aralkyl substituents. Preferably, the amine has a boiling point less than about 150° C. at 1 mm. Any number of the substituents may be part of a cycloaliphatic, aromatic, or heterocyclic ring structure. The amine moiety may have multiple amine groups.

Thus, suitable amine salts include, but are not limited to, salts of ammonia, methylamine, ethylamine, diethylamine, triethylamine, dibutylamine, cyclohexylamine, morpholine, pyrrolidine, piperidine, pyridine, piperazine, aniline, N-ethylaniline, N,N-dimethylaniline, benzylamine, N-ethylbenzylamine, ethylenediamine, and the like, and mixtures thereof.

Suitable amine salts have the formula $R_3NH+X-$ in which R is as described above, and $X-$ is an anion of a volatile acid. Thus, $X-$ may be, for example, a halide such as bromide or chloride, or an anion such as methanesulfonate, trifluoroacetate, or trifluoromethanesulfonate.

Thus, amine salts useful in the invention include, but are not limited to, ammonium chloride, ammonium bromide, methylammonium bromide, diethylammonium chloride, dibutylammonium trifluoromethanesulfonate, trimethylammonium trifluoroacetate, morpholine hydrochloride, pyridinium hydrochloride, anilinium hydrobromide, and the like.

A volatile acid as defined herein has a $pK_a$ less than about 3, and a boiling point less than about 150° C. at 1 mm. Typically, the $pK_a$ of the volatile acid is within the range of about 1 to about −15. In addition, the boiling point of the volatile acid is less than the thermal decomposition temperature of the amine/non-volatile acid salt. Examples of suitable volatile acids are hydrogen chloride, hydrogen bromide, hydrogen iodide, hydrogen fluoride, formic acid, hydrogen sulfide, hydrogen selenide, sulfur dioxide, fluorosulfonic acid, methanesulfonic acid, trifluoroacetic acid, trifluoromethanesulfonic acid, and the like.

Non-volatile acids useful in the process of the invention are capable of displacing the volatile acid from the amine salt of the volatile acid, and have a boiling point greater than the decomposition temperate of the amine/non-volatile acid salt. The non-volatile acid typically is less acidic than the volatile acid, and may be up to about $10^{10}$ times less acidic than the volatile acid. For example, if the $pK_a$ of the volatile acid is about −7 (like HCl), then the non-volatile acid will have a $pK_a$ within the range of about −7 to about 3. Preferred non-volatile acids have a $pK_a$ within the range of about 0 to about 4. The boiling point of the non-volatile acid will be greater than the decomposition temperature of the amine/non-volatile acid salt. Typically, the boiling point of the non-volatile acid will be greater than about 150° C. at atmospheric pressure.

Suitable non-volatile acids include phosphorus-containing acids such as, for example, ortho-phosphoric acid, pyrophosphoric acid, meta-phosphoric acid, polyphosphoric acid, alkyl- and aryl-substituted phosphonic and phosphinic acids, phosphorous acid, and the like, and mixtures thereof. Other suitable non-volatile acids include, but are not limited to, citric acid, oxalic acid, halogenated acetic acids, arene sulfonic acids, molybdic acid, phosphotungstic acid, tungstic acid, chromic acid, sulfamic acid, and the like.

In one embodiment of the invention, the non-volatile acid is slurried with or supported on an inert support. Suitable inert supports include, but are not limited to, diatomaceous earth, magnesium silicate, Kieselguhr, Attapulgus clay, alumina, silica gel, silica-aluminas, montmorillonite, and the like. The supported non-volatile acid reacts with the amine salt of a volatile acid to liberate the volatile acid in the usual way, and the amine is also easily recovered by heating the supported amine/non-volatile acid salt at elevated temperature. The ability to use a supported non-volatile acid adds flexibility to the process design.

The process of the invention involves two key steps. First, an amine salt of a volatile acid is reacted with a non-volatile acid at a temperature within the range of about 20° C. to about 220° C., preferably from about 80° C. to about 175° C. as the reaction proceeds, the volatile acid is liberated and is recovered by any suitable means, including distillation. The reaction product is the salt of an amine and a non-volatile acid. In a second step, this amine/non-volatile acid salt is heated, preferably at a temperature within the range of about 100° C. to about 350° C., to thermally decompose the salt and liberate the amine. A more preferred range is from about 160° C. to about 325° C. The amine, which is more volatile than the non-volatile acid, is recovered by any suitable means, including distillation. The non-volatile acid may be recovered and reused to convert additional amine salts to volatile acids and amines.

In practice, there is more latitude in operating conditions if not all of the amine/non-volatile acid salt is converted to the non-volatile acid and amine. Instead of returning pure non-volatile acid to the first stage of the reactor, it is convenient to return a mixture of recovered non-volatile acid and unconverted amine/non-volatile acid salt. The recycled components are combined with fresh amine salt of a volatile acid, and fresh non-volatile acid if desired.

The recovery of HCl (volatile acid) and diethylamine from diethylammonium hydrochloride (amine salt) using phosphoric acid (non-volatile acid) illustrates the invention (Scheme 1):

the reaction mixture. Examples of suitable salts of non-volatile acids that may be used include, but are not limited to, potassium dihydrogen phosphate, disodium hydrogen phosphate, sodium oxalate, sodium trichloroacetate, calcium tungstate, sodium citrate, and the like, and mixtures thereof.

Optionally, a solvent may be used to extract the non-volatile acid from the thermal decomposition mixture to assist recovery of the amine from the non-volatile acid salt. Generally, the extracting solvent is a good solvent for the non-volatile acid, but a relatively poor solvent for the amine/non-volatile acid salt. Preferred extracting solvents are aliphatic alcohols such as n-butyl alcohol and n-pentyl alcohol, ethers such as tetrahydrofuran, or glycol ethers, such as propylene glycol methyl ether.

The extraction mixture, which contains solvent and non-volatile acid, can be separated by any suitable means, including distillation. The recovered solvent can be reused in the extraction step. The recovered non-volatile acid, which may still contain some solvent, can be recycled to the first step.

The process of the invention may be performed using any suitable reactor. The process may be performed batchwise, semi-batchwise, or continuously, as desired, although continuous operation is preferred. A typical set-up will include a reaction vessel, means for heating the vessel, and separate collecting means for the volatile acid and the amine. The reaction mixture may be agitated if desired by any suitable means. In a preferred method, a thin film of the molten salt mixture is sprayed, dripped, and/or spread onto a hot surface from which the volatile products are easily separated. A wiped-film evaporator or a spiral-tube reactor may be used effectively to separate products. A wiped-film evaporator is

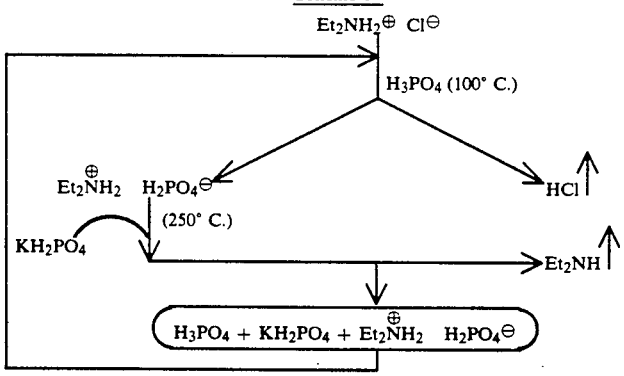

Scheme 1

Combination of diethylammonium chloride and phosphoric acid at 100° C. liberates hydrochloric acid, which distills overhead. The resulting diethylammonium dihydrogen phosphate salt is heated to 250° C. to release diethylamine and phosphoric acid. Water and acid condensates such as pyrophosphoric and polyphosphoric acids may also be formed. Recovery of the amine may be assisted by including potassium dihydrogen phosphate in the process. Water, non-volatile acids, and salts are returned to the first stage of the reactor. With recycle under steady-state conditions, essentially quantitative recovery of the volatile acid and amine can be achieved.

Recovery of amines from the amine/non-volatile acid salts can be assisted, if desired, by adding an alkali metal or alkaline earth metal salt of the non-volatile acid to preferred.

The process of the invention may be performed at, above, or below atmospheric pressure, as desired. An inert gas may be used to keep moisture out or to direct the flow of reaction products in a desired way. Nitrogen, argon, and the like are suitable inert gases.

If desired, the process of the invention may be performed in the presence of an inert solvent. It is preferred, however, to perform the process in the absence of a solvent, and at a temperature high enough to maintain a molten reaction mixture.

The following examples merely illustrate the invention. Those skilled in the art will recognize numerous variations that are within the spirit of the invention and scope of the claims.

EXAMPLE 1

Recovery of HCl and Diethylamine from Diethylamine Hydrochloride

Diethylamine hydrochloride (11 g, 100 mmol), o-phosphoric acid (30 g, 306 mmol) and potassium dihydrogen phosphate (13.6 g, 100 mmol) are charged to a 100-mL 3-neck round-bottom flask equipped with a magnetic stirring bar, a nitrogen gas inlet, and a product gas outlet. The nitrogen gas is introduced into the molten reaction mixture below the surface through a coarse frit. Gaseous reaction products and nitrogen carrier gas are removed through the product gas outlet, which is above the surface of the mixture. The product gas mixture is passed through an empty trap in which any condensable liquids may be separated from the product gas. After passing through the trap, the product gas containing HCl is collected for analysis using an aqueous scrubber, and the amount of HCl generated is measured by titrating the aqueous scrubber solution with 2N aqueous sodium hydroxide solution. The mixture is heated over 3 hours from an initial temperature of 100° C. to a final temperature of 135° C. with a continuous nitrogen sparge through the molten salt mixture. Recovery of HCl overhead as measured by titration is 99% based on the amount of diethylamine hydrochloride charged.

The same apparatus is used for recovering diethylamine in the second stage of the process. After HCl generation is complete, potassium dihydrogen phosphate (123 g) is added to the reaction mixture, which is then heated to 250° C. for another 3 hours. The product gas, which now contains diethylamine, is taken overhead to the aqueous scrubber system and is quantified by titration with 2N HCl. Recovery of diethylamine is 85%.

EXAMPLES 2-6

Recover of HCl from Diethylammonium Chloride

The apparatus described in Example 1 is used. Diethylammonium chloride is charged to the reactor along with a non-volatile acid and, optionally, an alkali metal salt, and the mixture is heated to liberate hydrogen chloride. Reaction conditions and yields of hydrogen chloride are reported in Table 1.

TABLE 1

Recovery of Hydrogen Chloride from Diethylammonium Chloride

| Example # | DEA.HCl (g, mol) | Recovered DEA Salt (g, mol) | Acid (g, mol) | Salt (g, mol) | Time (h) | Temp (°C.) | % HCl recovered |
|---|---|---|---|---|---|---|---|
| 2 | (11, 0.10) | — | $H_3PO_4$ (30, 0.31) | — | 7.0 | 100-140 | 78 |
| 3 | (11, 0.10) | — | $H_3PO_4$ (30, 0.31) | $KH_2PO_4$ (13.6, 0.1) | 2.5 | 90-140 | 99 |
| 4 | (11, 0.10) | — | $PhPO(OH)_2$ (28, 0.18) | — | 7.0 | 140 | 48 |
| 5 | (11, 0.10) | — | $H_4P_2O_7$ (30, 0.17) | — | 2.0 | 90-150 | 98 |
| 6 | (11, 0.10) | $DEA.H_4P_2O_7$ (7.0, 0.030) | $H_4P_2O_7$ (30, 0.17) | $KH_2PO_4$ (5, 0.04) | 3.0 | 120-135 | 90 |

EXAMPLES 7-16

Recovery of Diethylamine from Diethylammonium Salts

The apparatus described in Example 1 is used. Diethylammonium salts of various non-volatile acids are charged to the reactor along with other salts and/or additional acid, and the mixtures are heated to liberate diethylamine. Yields of diethylamine are reported in Table 2.

EXAMPLE 17

Two-Stage Recovery of Diethylamine and Hydrogen Chloride

A small-tube reactor having a 10-mL capacity is used. The tube is equipped with a nitrogen inlet tube that extends below the reaction mixture, and a product gas exit tube that leads to a trap and scrubber system for analyzing the product gases. The tube is heated by immersion in a constant-temperature oil bath. Diethylamine pyrophosphate (5.0 g, 20 mmol) is charged to the tube, and is heated for 2 h at 270° C. The diethylamine generated, determined by titration to be 4.4 mmol, is collected overhead. The reaction mixture is cooled, and then diethylammonium chloride (0.35 g, 3.2 mmol) is added. The mixture is heated at 150° C. for 2 h. The hydrogen chloride generated, 3.0 mmol as determined by titration, is collected overhead. The mixture is heated at 270° C. for another 2 h to recover 4 mmol of diethylamine. This cycle can be continued by adding a fresh charge of 0.35 g diethylammonium chloride.

TABLE 2

Recovery of Diethylamine from Diethylammonium Salts

| Example # | DEA salt (g, mol) | Other salt (g, mol) | Free acid (g, mol) | Time (h) | Temp. (°C.) | % DEA Recovered |
|---|---|---|---|---|---|---|
| 7 | $DEA.H_3PO_4$ (20, 0.12) | — | — | 2.0 | 240-310 | 58 |
| 8 | $DEA.H_3PO_4$ (6, 0.35) | $KH_2PO_4$ (24, 0.18) | — | 1.2 | 250 | 94 |
| 9 | $DEA.H_3PO_4$ (12, 0.70) | $KH_2PO_4$ (19, 0.14) | — | 1.4 | 270 | 90 |
| 10 | $DEA.PhPO(OH)_2$ (28.6, 0.12) | — | — | 1.6 | 250 | 63 |
| 11 | $DEA.H_3PO_4$ (17, 0.10) | $K_2HPO_4$ (175, 1.0) | $H_3PO_4$ (30, 0.30) | 3.0 | 250 | 86 |
| 12 | $DEA.H_3PO_4$ (17, 0.10) | $KH_2PO_4$ (135, 1.0) | $H_3PO_4$ (30, 0.30) | 3.5 | 250 | 90 |

TABLE 2-continued

Recovery of Diethylamine from Diethylammonium Salts

| Example # | DEA salt (g, mol) | Other salt (g, mol) | Free acid (g, mol) | Time (h) | Temp. (°C.) | % DEA Recovered |
|---|---|---|---|---|---|---|
| 13 | DEA.$H_3PO_4$ (17, 0.10) | $K_2HPO_4$ (55, 0.30) | $H_3PO_4$ (30, 0.30) | 7.0 | 240 | 72 |
| 14 | DEA.$H_3PO_4$ (17, 0.10) | $K_4P_2O_7$ (17, 0.05) | — | 3.5 | 250 | 97 |
| 15 | DEA.$H_3PO_4$ (34.6, 0.20) | $K_4P_2O_7$ (17, 0.05) | — | 4.0 | 250 | 92 |
| 16 | DEA.$H_4P_2O_7$ (8.3, 0.033) | $KH_2PO_4$ (7.5, 0.055) | — | 5.0 | 240-330 | 68 |

EXAMPLE 18

Recover of HCl from Diethylammonium Chloride Wiped-Film Evaporator Technique

A suitable glass-shell wiped-film evaporator, such as those manufactured by Pope Scientific, is used to provide a short residence time in a thin-film reactor with continuous feed of the molten salt. The 2"-diameter shell is heated with an external heating mantle. The molten salt mixture, which comprises diethylammonium chloride (21.8 g, 0.2 mol) and pyrophosphoric acid (42.8 g, 0.24 mol), is fed to the reactor by gravity flow from a heated addition funnel. Nitrogen is introduced from the bottom of the unit to help sweep liberated hydrogen chloride overhead. The hydrogen chloride is collected for analysis using an aqueous scrubber, and is measured by titration with standard aqueous sodium hydroxide solution. The product is collected from a bottom take-off, and is analyzed for residual chlorine content. Some hydrogen chloride is generated in the heated addition funnel, and is not collected in the overhead scrubber system Consequently, the residual chlorine analysis of the nonvolatile product is a more accurate measure of HCl removal. The wall temperature is maintained at 130° C., and the feed rate is adjusted to give a residence time in the reactor of about 5 min. Recovery of HCl as measured by titration is 90%. Residual chlorine in the reactor product is 0.05 wt. %, which corresponds to 99.5% chlorine removal.

EXAMPLES 19-22

Recovery of Hydrochloric Acid from Diethylamine Hydrochloride using Ortho-Phosphoric Acid ($H_3PO_4$)

The procedure of Example 18 is followed using a molten salt mixture of diethylammonium chloride and o-phosphoric acid in the mole ratios listed in Table 3. The rector temperature, amount of HCl recovered overhead, and HCl removal as calculated from residual chlorine content of the reaction product are also recorded in Table 3.

EXAMPLE 23

Recovery of Diethylamine from Diethylammonium Phosphate/Phosphoric Acid

The apparatus and procedure of Example 18 is followed, except that the addition funnel is maintained at about 130° C. to keep the salt molten, and a heated fluid is circulated through the internal condenser of the wiped-film evaporator to help vaporize the liberated diethylamine. A mixture of diethylammonium phosphate and phosphoric acid (1/0.5 molar ratio) containing about 33 wt. % of diethylamine (made, for example, by the methods of examples 1 and 18) is fed into the wiped-film evaporator with a wall temperature of 270° C. The overhead product is recovered using an aqueous scrubber solution, and the amount of diethylamine recovered is determined by titration with standard acid. The feed rate to the WFE is adjusted to give a residence time of about 5 min. Overhead recovery of diethylamine is 34%. Diethylamine hydrochloride is added to the bottoms product to replace the diethylamine removed overhead. This product is recycled to the first stage wiped-film evaporator according to the procedure of example 18 to recover hydrogen chloride.

TABLE 3

(Examples 19-22)
Recovery of Hydrochloric acid from Diethylamine Hydrochloride using o-Phosphoric Acid

| Example # | Mole Ratio DEA.HCl/ $H_3PO_4$ | Temp. (°C.) | % HCl Overhead | % Cl product | % HCl Removed |
|---|---|---|---|---|---|
| 19 | 1.0/1.5 | 130 | 72 | 5.0 | 64 |
| 20 | 1.0/1.5 | 165 | 70 | 3.5 | 74 |
| 21 | 1.0/1.5 | 200 | 80 | 2.5 | 82 |
| 22 | 1.0/2.0 | 150 | 87 | 0.6 | 95 |

% HCl Overhead = Amount of HCl recovered in aqueous scrubber system as measured by titration with standard aqueous NaOH.
% Cl Product = Weight percent of Cl by elemental analysis of the pot residue following heat treatment in the wiped-film evaporator.
% HCl Removed = Amount of HCl removed from the salt based on residual chloride analysis.

EXAMPLE 24

The procedure of Example 23 is followed using a feed mixture of diethylammonium phosphate and phosphoric acid (1/0.5 molar ratio), except that the wall temperature is maintained at 325° C. Overhead recovery of diethylamine is 49%. The remaining product, a mixture of unconverted diethylammonium phosphate with phosphoric acid and condensed phosphoric acids, is recycled to the wiped-film evaporator with a fresh charge of diethylamine hydrochloride, so that the charge composition is 0.5 mol DEA.$H_3PO_4$/1.0 mol $H_3$/$PO_4$/0.5 mol DEA.HCl, to recover HCl from the added DEA.HCl by the methods of Examples 18-22.

EXAMPLE 25

A mixture of diethylammonium phosphate (51 g, 0.30 mol) and water (6 g, 0.3 mol) is charged to the wiped-film evaporator using a wall temperature of 270° C. Recovery of diethylamine overhead is 71%.

EXAMPLE 26

Multiple-batch Process for Recovery of HCl and DEA Pyrophosphoric Acid Recovery by 1-Pentanol Extraction Step 1: A one-liter reaction kettle equipped with a mechanical stirrer, thermometer, and nitrogen inlet tube that can be adjusted either above or below the surface of the reaction mixture are used. A condenser, which can be chilled or heated as desired, is fitted with a distillation head and round-bottom receiver. The exit tube from the distillation head leads to a water scrubber system for recovery and analysis by titration of either hydrogen chloride or diethylamine. In step 1, a mixture of diethylammonium pyrophosphate (138 g, 0.55 mol), potassium dihydrogen phosphate (106 g, 0.78 mol) and water (38 g, 2.1 mol) is heated at 295° C. for 4 h. Diethylamine (23 g, 0.31 mol) is recovered overhead (56% of the amount charged as pyrophosphate salt).

Step 2: A mixture of diethylammonium chloride (35 g, 0.32 mol) and pyrophosphoric acid (125 g, 0.73 ml) is added to 203 g of the reaction product from Step 1. This mixture is heated at 140° C. for 5 h. Hydrochloric acid removal is 94% based on the amount recovered overhead as measured by titration, and 98% based on chloride analysis of the pot residue.

Step 3: The pot residue from step 2 is extracted with 1-pentanol (3×550 g) to recover excess pyrophosphoric acid. An aliquot of the salt phase is heated to 300° C. for 3 h. Ninety percent of the diethylamine is removed overhead based on titration of the scrubber solution, and also based on percent nitrogen analysis of the pot mixture before and after heating. The bulk of the salt phase is heated at 300° C. for 3.5 h, and 70% of the diethylamine is taken overhead. (The larger scale batch operation is somewhat less efficient than the smaller scale run because of problems with mixing, heat transfer, and nitrogen sparging on the larger scale.) The pyrophosphoric acid can be recovered for reuse from the 1-pentanol extracts as shown in Example 29.

Step 4: The cycle is repeated by adding diethylammonium chloride (49.4 g, 0.45 mol) and pyrophosphoric acid (127 g) to the product from Step 3. After heating at 140° C. for 4 h, removal of hydrogen chloride is 93% as measured by titration.

EXAMPLE 27

Attapulgus Clay as a Support for Phosphoric Acid Recovery of HCl and DEA from DEA.HCl Phosphoric acid (85%) (50 mL) and distilled water (350 mL) are combined with Attapulgus clay (16/30 mesh) (100 g) and mixed well until the clay is saturated with the aqueous acid. Excess water is removed in vacuo using a rotary evaporator. The resulting solid is then heated at 110° C. for 2 h. Diethylammonium chloride (2.14 g) in methanol (50 mL) is added to the acid-treated clay (20 g), followed by hexadecane (100 mL). Methanol is removed from the mixture by distillation. The suspension of clay in hexadecane is heated to 140° C., and HCl is liberated. Recovery of HCl, as measured by titration of the overhead vapor, is 74%. When the slurry is heated to 270° C., about 20% of the diethylamine is released.

EXAMPLE 28

Diatomaceous Earth as a Support for Phosphoric Acid Recovery of HCl from DEA.HCl The procedure of Example 27 is followed to support phosphoric acid on diatomaceous earth. Diethylammonium chloride (2.06 g) in water is added to the acid-treated diatomaceous earth (20 g). The mixture is heated at 120° C., and HCl is recovered overhead in 91% yield.

EXAMPLE 29

Recovery and Reuse of Pyrophosphoric Acid

Step 1: Diethylammonium chloride (21.9 g, 0.20 mol) is combined with potassium dihydrogen phosphate (27.6 g, 0.20 mol), pyrophosphoric acid (82 g, 0.46 mol), and 1-pentanol (68 g). The mixture is heated at 130° C. until evolution of HCl cases. Analysis of the reaction pot reveals that less than 60 ppm chloride is present. Additional 1-pentanol (210 g) is added to extract the pyrophosphoric acid. The components are mixed at 90° C., and the phases are separated. The salt phase is set aside for diethylamine recovery. Pyrophosphoric acid is recovered from the 1-pentanol phase for recycle as described in Step 2.

Step 2: The 1-pentanol phase from the single-stage extraction (Step 1) contains 41 g (0.23 mol) of pyrophosphoric acid. 1-Pentanol is removed from this phase in vacuo using a rotary evaporator. The residue, which contains pyrophosphoric acid (40.1 g) and 1-pentanol (60 g), is used in Step 3 to treat a new batch of diethylammonium chloride. The 1-pentanol collected in the evaporator is recycled to the extraction step.

Step 3: The pot residue from Step 2, which contains 40 g pyrophosphoric acid, is combined with diethylammonium chloride (22.7 g), potassium dihydrogen phosphate (28 g), and make-up pyrophosphoric acid (43 g). The mixture is heated at 130° C. until HCl no longer evolves. Analysis of the pot again reveals less than 60 ppm chloride. Additional 1-pentanol (210 g) is added, the components are mixed at 90° C., and the phases are separated. The salt phase is sent forward for diethylamine recovery. Pyrophosphoric acid is again recovered from the 1-pentanol phase for recycle. The entire process is repeated a third time. (In practice, a staged extraction with 1-pentanol would be performed to increase pyrophosphoric acid recovery in Step 2, and the make-up pyrophosphoric acid and potassium dihydrogen phosphate would be recycled from the diethylamine recovery step.)

We claim:

1. A process for recovering an amine and a volatile acid from an amine salt, said process comprising: (a) reacting an amine salt with a non-volatile acid at a temperature within the range of about 20° C. to about 220° C. to form an amine/non-volatile acid salt while liberating the volatile acid; and (b) heating the amine/non-volatile acid salt at a temperature within the range of about 100° C. to about 350° C. to liberate the amine; wherein the volatile acid has a boiling point less than about 150° C. at 1 mm; and wherein the non-volatile acid has a boiling point greater than about 150° C. at atmospheric pressure, and is up to about $10^{10}$ times less acidic than the volatile acid.

2. The process of claim 1 wherein the amine salt is derived from an amine having from 0 to 3 linear, branched, or cyclic alkyl, aryl, or aralkyl substituents.

3. The process of claim 1 wherein the amine salt is derived from an amine selected from the group consisting of ammonia, alkylamines, dialkylamines, trialkylamines, morpholine, pyrrolidine, piperidine, pyridine, piperazine, aniline, N-substituted anilines, benzylamine, and ethylene diamine.

4. The process of claim 1 wherein the amine salt is derived from a volatile acid that has a $pK_a$ less than about 3.

5. The process of claim 1 wherein the amine salt is derived from a volatile acid selected from the group consisting of hydrochloric acid, hydrobromic acid, fluorosulfonic acid, methanesulfonic acid, trifluoroacetic acid, and trifluoromethanesulfonic acid.

6. The process of claim 1 wherein the non-volatile acid has a $pK_a$ within the range of about 0 to about 4.

7. The process of claim 1 wherein the non-volatile acid is selected from the group consisting of ortho-phosphoric acid, pyrophosphoric acid, meta-phosphoric acid, polyphosphoric acid, aryl- and alkyl-substituted phosphonic and phosphinic acids, phosphorous acid, citric acid, oxalic acid, halogenated acetic acids, arene sulfonic acids, molybdic acid, tungstic acid, chromic acid, sulfamic acid, and mixtures thereof.

8. The process of claim 1 wherein heating of the amine/non-volatile acid salt in step (b) of the process results in partial conversion to the amine, non-volatile acid, and unconverted amine/non-volatile acid salt; the amine is recovered; and the non-volatile acid and the unconverted amine/non-volatile acid salt are recycled to step (a) of the process.

9. The process of claim 1 wherein an alkali metal salt or alkaline earth metal salt of a non-volatile acid is included at step (b) of the process.

10. The process of claim 1 wherein excess non-volatile acid is removed by extraction into an aliphatic alcohol, ether, or glycol ether.

11. The process of claim 1 wherein the process is performed at a temperature sufficient to give a molten reaction mixture, and the molten reaction mixture is applied as a thin film to a hot reactor surface to facilitate removal of the volatile acid and the amine.

12. A process for recovering an amine and a volatile acid from an amine salt, said process comprising: (a) reacting an amine salt with a non-volatile acid at a temperature within the range of about 20° C. to about 220° C. to form an amine/non-volatile acid salt while liberating the volatile acid; and (b) heating the amine/non-volatile acid salt at a temperature within the range of about 100° C. to about 350° C. to liberate the amine;

wherein the volatile acid has a $pK_a$ within the range of about 1 to about −15 and a boiling point less than about 150° C. at 1 mm; and wherein the non-volatile acid has a $pK_a$ within the range of about 0 to about 4 and a boiling point greater than about 150° C. at atmospheric pressure.

13. The process of claim 12 wherein the amine salt is derived from an amine having from 0 to 3 linear, branched, or cyclic alkyl, aryl, or aralkyl substituents.

14. The process of claim 12 wherein the amine salt is derived from an amine selected from the group consisting of ammonia, alkylamines, dialkylamines, trialkylamines, morpholine, pyrrolidine, piperidine, pyridine, piperazine, aniline, N-substituted anilines, benzylamine, and ethylene diamine.

15. The process of claim 12 wherein the amine salt is derived from a volatile acid selected from the group consisting of hydrochloric acid, hydrobromic acid, fluorosulfonic acid, methanesulfonic acid, trifluoroacetic acid, and trifluoromethanesulfonic acid.

16. The process of claim 12 wherein the non-volatile acid is selected from the group consisting of ortho-phosphoric acid, pyrophosphoric acid, meta-phosphoric acid, polyphosphoric acid, aryl- and alkyl-substituted phosphonic and phosphinic acids, phosphorous acid, citric acid, oxalic acid, halogenated acetic acids, arene sulfonic acids, molybdic acid, tungstic acid, chromic acid, sulfamic acid, and mixtures thereof.

17. The process of claim 12 wherein heating of the amine/non-volatile acid salt in step (b) of the process results in partial conversion to the amine, non-volatile acid, and unconverted amine/non-volatile acid salt; the amine is recovered; and the non-volatile acid and the unconverted amine/non-volatile acid salt are recycled to step (a) of the process.

18. The process of claim 12 wherein an alkali metal salt or alkaline earth metal salt of a non-volatile acid is included at step (b) of the process.

19. The process of claim 12 wherein excess non-volatile acid is removed by extraction into an aliphatic alcohol, ether, or glycol ether.

20. The process of claim 12 wherein the process is performed at a temperature sufficient to give a molten reaction mixture, and the molten reaction mixture is applied as a thin film to a hot reactor surface to facilitate removal of the volatile acid and the amine.

* * * * *